United States Patent
Grimm

(12) 
(10) Patent No.: US 6,264,600 B1
(45) Date of Patent: Jul. 24, 2001

(54) HOLLOW SUTURE MEMBER WITH RADIOACTIVE SEEDS POSITIONED THEREIN FOR TREATMENT OF PROSTATE CANCER

(76) Inventor: Peter D. Grimm, 1211 E. Newton, Seattle, WA (US) 98102

( * ) Notice: Subject to any disclaimer, the term of this patent is extended or adjusted under 35 U.S.C. 154(b) by 0 days.

(21) Appl. No.: 09/426,068

(22) Filed: Oct. 21, 1999

(51) Int. Cl.$^7$ ................................................. A61M 36/12
(52) U.S. Cl. ..................................................... 600/7; 600/3
(58) Field of Search ................................ 600/3, 4, 7, 8; 724/1.11; 606/130

(56) References Cited

U.S. PATENT DOCUMENTS

| | | | |
|---|---|---|---|
| 4,697,575 | * 10/1987 | Horowitz | 600/8 |
| 4,957,476 | * 9/1990 | Cano | 600/7 |
| 5,928,130 | * 7/1999 | Schmidt | 600/7 |
| 5,938,583 | * 8/1999 | Grimm | 600/7 |
| 6,010,446 | * 1/2000 | Grimm | 600/3 |
| 6,159,143 | * 12/2000 | Lennox | 600/4 |

OTHER PUBLICATIONS

A. Vant't Riet et al "Ultrasonically Guided Transperineal Seed Implantation of the Prostate: Modification of the Technique and Qualitative Assessement of Implants", Int'l J. Radiation Oncology Biol. Phys., vol. 24, pp. 555–558, 1992 #3.

* cited by examiner

Primary Examiner—Eric F. Winakur
Assistant Examiner—Nikita R Veniaminov
(74) Attorney, Agent, or Firm—Jensen & Puntigam, P.S.

(57) ABSTRACT

The method and apparatus includes a length of hollow suture material in which an alternating plurality of radioactive seeds and intermediate spacers are located. The suture member includes a portion which extends a substantial distance beyond the first radioactive seed in the suture member. The combination of the hollow suture member, the radioactive seeds and spacers is then moved into a insertion needle through a hub end thereof, to the point where the free end of the hollow suture member extends past the tip end of the insertion needle. The suture member then is pulled through the hollow insertion needle until the first radioactive seed in the suture member is positioned at the tip end of the insertion needle. The extended portion of the hollow suture member is then severed in the vicinity of the tip end of the insertion needle. The loaded insertion needle is then inserted into the prostate of the patient.

11 Claims, 1 Drawing Sheet

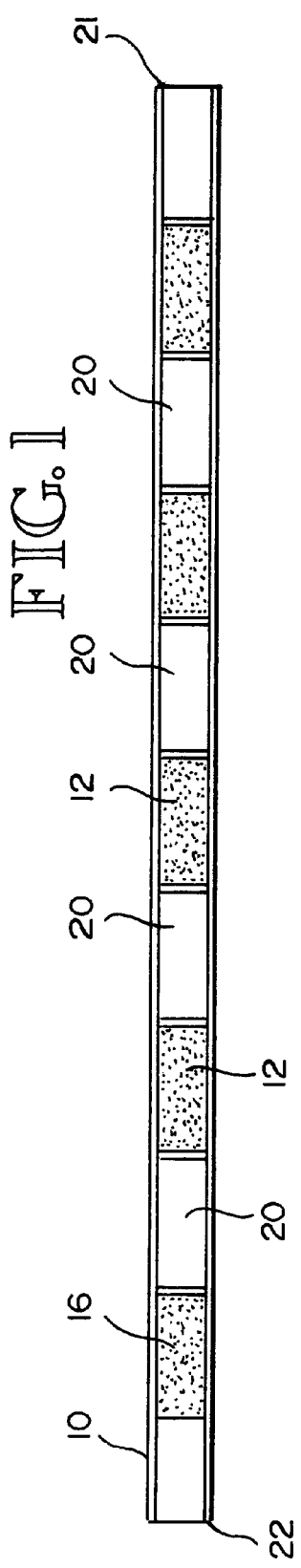
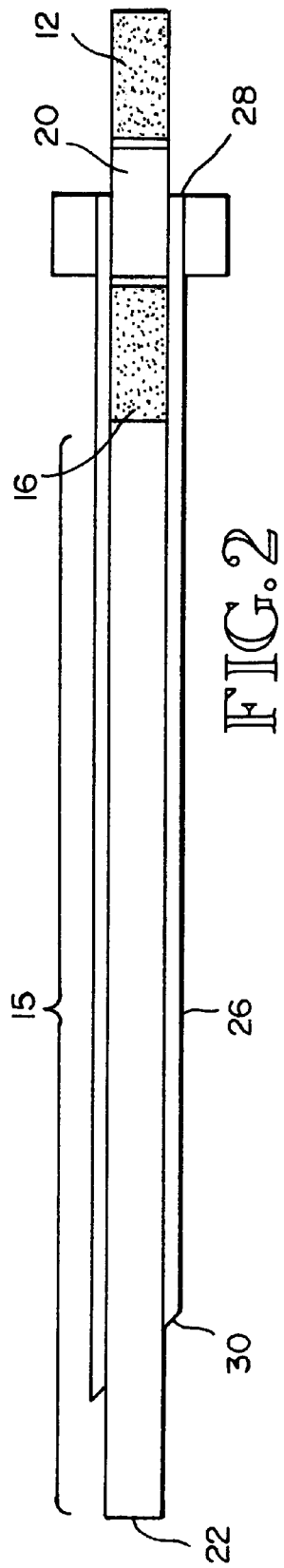
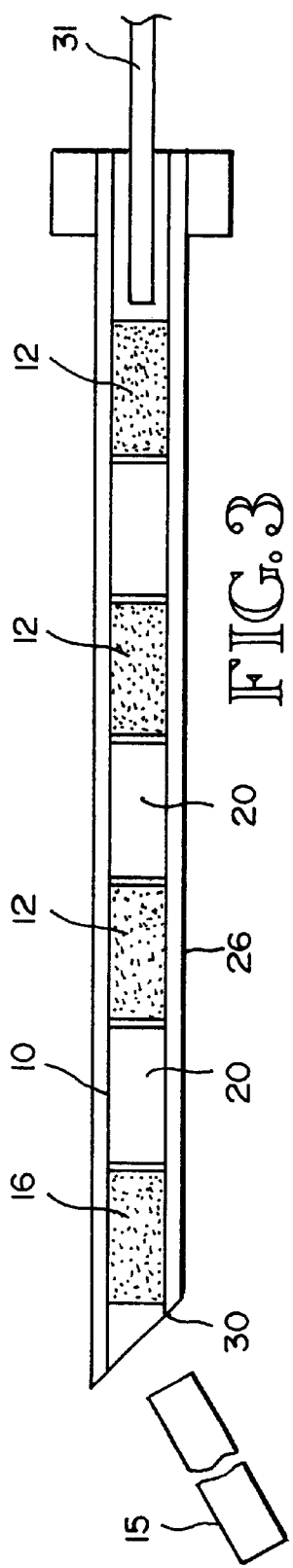

HOLLOW SUTURE MEMBER WITH RADIOACTIVE SEEDS POSITIONED THEREIN FOR TREATMENT OF PROSTATE CANCER

TECHNICAL FIELD

This invention relates generally to radioactive seed implantation treatment of prostate cancer, and more specifically concerns a structure for implanting the radioactive seeds in the prostate.

BACKGROUND OF THE INVENTION

Radioactive seed implantation treatment of prostate cancer, known as brachytherapy, is an increasingly popular and effective treatment for prostate cancer. In the brachytherapy technique, radioactive seeds are loaded into hollow needles, with the needles then being inserted into the prostate, using ultrasound imaging to guide the insertion process. The radioactive seeds are either positioned independently (not connected) within the needles and hence are located independently within the prostate after they have been moved out of the needle, or they are connected in a string arrangement by being loaded within a hollow, absorbable suture member, such as Vicryl suture.

In the suture arrangement, the individual radioactive seeds positioned therein are spaced apart, typically 1 cm. After the suture is filled with radioactive seeds, it is heated in a fixture to stiffen the suture and stabilize the position of the radioactive seeds therein. Typically, each suture arrangement has a length sufficient to accommodate at least ten radioactive seeds.

The hollow suture/radioactive seed combination was a significant improvement over the independently (unconnected, spaced seed approach, since the independent seeds, even once located in the prostate, could migrate out of the prostate to various other locations in the body, including the lungs. Migrated seeds can reduce implant quality and also potentially harm the patient.

While the hollow suture combination is a significant improvement to the independent seed arrangement, there are disadvantages to the suture combination approach. The heating step which is used to stiffen the suture combination, a necessary step in the process, can degrade the suture material. The suture combination also sometimes jams within the insertion needle, resulting in a collapsing or buckling of the suture combination. This in turn requires removal of the needle from the prostate and the subsequent reloading of the needle with independently positioned seeds. This is a time-consuming and expensive process. In addition, the commonly available ten seed per suture arrangement necessary to fit available fixtures often results in wasted radioactive seeds when seeds are required for a particular implant.

Further, the free end tips of the insertion needles must be plugged prior to the loading of the suture combination into the insertion needle, again a time-consuming process.

Hence, it is desirable to have a radioactive seed/suture arrangement which is simple, does not require a heating step, and which is more reliable in use than current suture embodiments.

DISCLOSURE OF THE INVENTION

Accordingly, the present invention is a combination of a hollow suture member and a plurality of radioactive seeds located therein for use in treatment of prostate cancer, comprising: a hollow suture member; and a plurality of radioactive seeds positioned therein, separated from each other by spacer members, wherein the suture member includes a portion which extends beyond a first radioactive seed position in the suture a substantial distance, wherein the combination is ready for insertion into a hollow insertion needle.

BRIEF DESCRIPTION OF THE DRAWINGS

FIG. 1 is a cross-sectional view of the improved suture combination of the present invention.

FIG. 2 shows the loading of the suture combination of the present invention into an insertion needle.

FIG. 3 shows an insertion needle loaded with the suture combination of the present invention, ready to be inserted into a patient's prostate.

BEST MODE FOR CARRYING OUT THE INVENTION

FIG. 1 shows the radioactive seed suture combination of the present invention. The combination is used in the radioactive seed implantation treatment of prostate cancer, which is explained in detail in U.S. Pat. No. 5,938,583, to Peter Grimm. The suture is a conventional absorbable suture member 10, having an internal diameter sufficient to accommodate a plurality of radioactive seeds 12—12, which typically, but not necessarily, are approximately 0.8 mm in diameter and 4.5 mm long. The suture member material is conventional. However, suture member 10 is substantially longer than conventional suture members which are capable of carrying 10 or more radioactive seeds. In the present invention, the length of portion 15 of suture member 10 which extends from the first radioactive seed 16 in the suture member to the free end 22 of the suture member is a substantial distance. In the embodiment shown, it is approximately equal to the length of the hollow insertion needle.

Positioned within suture member 10 are a plurality of spaced radioactive seeds 12—12, separated by individual spacer members 20—20. The number of radioactive seeds in the suture member could be any selected number, in accordance with the particular requirement of the implant. The individual spacer members 20—20 maintain a known separation between adjacent radioactive seeds and produce a sequential, spaced positioning of the radioactive seeds 12 within suture member 10. In the embodiment shown, spacer members 20 have approximately the same diameter as the radioactive seeds 12 and are also approximately the same length, although this is not necessary to the present invention.

The suture material in the embodiment shown is opaque or almost clear so that the seeds and spacers in the suture can be seen. Also, the suture length can be pre-marked to indicate the correct position in the suture for the radioactive seeds and spacers.

In the use of the suture combination of the present invention, radioactive seeds 12 and spacer members 20 are moved alternately into suture member 10 from a loading end 21, but only to the point where the innermost radioactive seed 16 is a selected substantial distance from free end 22 of suture member 10. Once the desired number of radioactive seeds and spacers are in place in the suture member, the combination of the suture member, the radioactive loaded seeds and the spacer members is ready to be loaded into a hollow insertion needle 26. The suture member with seeds and spacers does not require a heating or other stiffening step.

The suture member with seeds and spacers is then loaded into a hollow insertion needle 26, as shown in FIG. 2, through a hub end 28 thereof. Free end 22 of suture member 10 is moved through insertion needle 26 until the free end exits tip end 30 of the insertion needle 26.

Free end 22 of suture 10 member is then pulled through insertion needle 26 until the first radioactive seed 16 in the suture member is in the vicinity of tip end 30 of the insertion needle 26. The portion of the suture member from the first radioactive seed 16 to the free end thereof is then severed by a knife or the like. The loaded insertion needle is now ready to be inserted into the prostate of the patient.

After the loaded needle has been inserted, a stylet 31 (FIG. 3) is used to push the suture member, with seeds and spacers therein, into the prostate. When this is completed, the insertion needle and stylet 31 are removed from the prostate, leaving the suture member with seeds and spacers in place in the prostate. The radioactive seeds thus have been placed in a precisely arrayed line, in a particular spaced relationship relative to each other. The seeds are prevented from migrating via the suture member and thus maintain their original alignment in the prostate.

The present invention is advantageous over conventional suture member/seed combinations, since it does not require any heating for stability or other reasons and thus requires no special fixtures to accomplish such heating. Further, the insertion needle does not need to be plugged at its tip end prior to insertion of the suture member, as the suture member initially is drawn out through the open tip end of the insertion needle. Further, the presence of the spacers tends to prevent the suture member from buckling, which in turn reduces the likelihood of the combination of the suture member and the seeds jamming in the insertion needle.

The combination is also relatively inexpensive. Loading time and effort for both the suture member and the insertion needle is decreased, as are and in operating room time and costs. Hence, the present invention has significant advantages over the existing suture member/seed combination.

Although a preferred embodiment of the invention has been disclosed here for purposes of illustration, it should be understood that various changes, modifications and substitutions may be incorporated without departing from the spirit of the invention, which is defined by the claims which follow.

What is claimed is:

1. A combination of a hollow suture member and a plurality of radioactive seeds located therein for use in treatment of prostate cancer, comprising:
   a hollow suture member; and
   a string of a plurality of radioactive seeds positioned therein, separated from each other by spacer members, wherein the suture member includes a portion which extends beyond a first radioactive seed positioned at a forward end of said string of radioactive seeds a substantial distance of at least the length of one radioactive seed and spacer member, wherein the combination is adapted for insertion into a hollow insertion needle.

2. An article of claim 1, wherein the extended portion of the suture member is at least as long as the length of the insertion needle.

3. An article of claim 1, wherein the suture member is sufficiently clear that the seeds and spacers therein can be readily seen.

4. An article of claim 3, wherein the suture member is pre-marked to indicate proper position of the seeds and spacers within the suture member.

5. An article of claim 1, wherein the radioactive seeds comprise a preselected number of seeds, and wherein successive radioactive seeds are separated by successive spacer members, the spacer members tending to maintain the integrity of the suture member combination, preventing buckling of the suture member within the insertion needle.

6. A method of loading radioactive seeds into an insertion needle for use in the treatment of prostate cancer, the method comprising the steps of:
   loading radioactive seeds and spacers, with a spacer between successive seeds, into a hollow suture member, wherein the suture member includes a portion which extends a substantial distance beyond a first radioactive seed positioned in the suture member, from the first radioactive seed to a free end of the suture member;
   inserting the loaded suture member into a hub end of a hollow needle suitable for insertion into the prostate;
   moving the loaded suture member sufficiently through the insertion needle until said first radioactive seed in the suture member is approximately adjacent an opposing tip end of the hollow insertion needle; and
   severing the extended portion in the vicinity of the tip end of the insertion needle.

7. A method of claim 6, wherein the extended portion of the suture member is approximately at least equal to the length of the insertion needle.

8. A method of claim 7, wherein the radioactive seeds alternate with spacer members within the suture member, the spacer members tending to prevent buckling of the suture member during insertion of the loaded needle into the prostate.

9. A method of claim 6, wherein the number of radioactive seeds in the hollow suture member is preselected.

10. A method for loading radioactive seeds into an insertion needle and subsequent placement of the radioactive seeds in the prostate, the method comprising the steps of:
   loading radioactive seeds and spacers, with at least one spacer positioned between successive seeds, into a hollow suture member, wherein the suture member includes a portion which extends a substantial distance beyond the first radioactive seed positioned in the suture member, said portion extending from the first radioactive seed to a free end of the suture member;
   inserting the loaded suture member into a hub end of a hollow needle suitable for insertion into the prostate, wherein the step of loading the radioactive seeds and spacers into the hollow suture member occurs prior to the insertion of the loaded suture member into the hub end of the hollow insertion needle;
   moving the loaded suture member sufficiently through the insertion needle until said first radioactive seed in the suture member is approximately adjacent an opposing tip end of the hollow insertion needle;
   severing the extended portion of the suture member from the remainder of the suture member in the vicinity of the tip end of the insertion needle;
   inserting the loaded needle into the prostate to a preselected position therein; and
   removing the needle from around the loaded suture member, leaving the loaded suture member in said preselected position in the prostate.

11. An article of claim 10, wherein the suture member is sufficiently clear that the seeds and spacers therein can be readily seen so that the first radioactive seed can be conveniently identified within the insertion needle during the step of moving.

* * * * *